United States Patent [19]

Makiguchi et al.

[11] Patent Number: 4,684,252

[45] Date of Patent: Aug. 4, 1987

[54] AUTOMATED ANALYZING APPARATUS

[75] Inventors: Kyoko Makiguchi; Hisayuki Sagusa, both of Katsuta; Yasushi Nomura, Mito, all of Japan

[73] Assignee: Hitachi, Ltd., Tokyo, Japan

[21] Appl. No.: 886,765

[22] Filed: Jul. 16, 1986

Related U.S. Application Data

[63] Continuation of Ser. No. 556,411, Nov. 30, 1983, abandoned.

[30] Foreign Application Priority Data

Dec. 1, 1982 [JP] Japan .................................. 57-209347

[51] Int. Cl.⁴ .......................... G01J 3/18; G01J 21/27
[52] U.S. Cl. ..................................... 356/328; 356/39; 356/442
[58] Field of Search .................... 356/39, 73, 326, 328, 356/442

[56] References Cited

U.S. PATENT DOCUMENTS

| | | | |
|---|---|---|---|
| 3,510,666 | 5/1970 | Topol | 250/574 |
| 3,819,271 | 6/1974 | Beug et al. | 356/39 |
| 3,827,805 | 8/1974 | Mansfield et al. | 356/73 |
| 4,027,973 | 6/1977 | Kaye | 356/73 |
| 4,167,335 | 9/1979 | Williams | 356/336 |
| 4,263,512 | 4/1981 | Sagusa et al. | 356/51 X |
| 4,313,735 | 2/1982 | Yamashita et al. | 364/498 X |
| 4,372,683 | 2/1983 | Sternberg | 356/338 |
| 4,423,331 | 12/1983 | Koizumi et al. | 356/446 X |

FOREIGN PATENT DOCUMENTS 0016322  1/1982  Japan ..................................... 356/73

Primary Examiner—Vincent P. McGraw
Attorney, Agent, or Firm—Antonelli, Terry & Wands

[57] ABSTRACT

An automated analyzing apparatus with a photometer including an entrance slit permitting passing therethrough of the entirety or a portion of a convergent light beam transmitted successively through a plurality of sample measurement cells each containing a sample solution therein and a sensor converting the quantity of light passed through the entrance slit into a physical quantity which is an objective of measurement. A scattered light sensor is disposed between the sample measurement cells and the entrance slit at a position where the sensor is not irradiated with a straight advancing component of the light beam, whereby measurement of immunity-related tests on the basis of the intensity of scattered light can be made together with measurement of biochemical tests on the basis of the intensity of transmitted light.

7 Claims, 7 Drawing Figures

AUTOMATED ANALYZING APPARATUS

This application is a continuation of application Ser. No. 556,411 filed Nov. 30, 1983.

This invention relates to an automated analyzing apparatus used for biochemical and other tests on samples, and more particularly to an apparatus of the kind above described which enables both the measurement of biochemical tests by sensing light transmitted through a sample and the measurement of immunochemical tests by sensing light scattered by the sample.

It has been clarified recently that quantitative analysis of antigens such as proteins, bacilli and viruses related to the immunity of a living body or of substances related to thromokinesis and fibrinolysis are required for therapeutic and preventative medicine. These substances are quantitatively determined by an immunochemical method due to its extremely high selectivity and sensitivity. As is well known, this method is classified into the following three methods:

(1) Method utilizing a defusion and sedimentation reaction in a gel

This first method is widely used by virtue of its simple procedure for measurement. However, it is defective in that a period of time longer than one day is required for the measurement and yet the quantitative analysis does not always provide an accurate result.

(2) Method using a labeled antigen-antibody

This second method is classified into, for example, an RIA (radioimmunoassay) method using a radioactive isotope and a fluoroimmunoassay method using a fluorescent compound. However, both of these methods are defective in that there is the necessity for consideration of the stability of reagents during measurement and that, because of the necessity for using a special apparatus for measurement, a conventional automated analyzing apparatus for biochemical tests cannot be substituted therefor.

(3) Method utilizing an agglutinating reaction in a solution:

This third method makes quantitative analysis of a combined product of an antigen (a sample) and an antibody (a reagent), which product is produced as a result of mixing of the antigen with the antibody, and thus obtained turbidity is quantitized by turbidometry or nephelometry is used for this purpose. They are disclosed respectively, *Clinical Chemistry* Vol. 28 No. 10 1982 p. 2121-2124. "Turbidimetric Immunoassay of Serum C-Reactive Protein" and *Journal of Immunological Methods* 5 (1974) p. 153-163 "Automated Nephelometric Immunoassay (ANIA) I. Importance of Antibody Affinity". In each of the turbidometry and nephelometry, the turbidity of the reaction solution attributable to the combined product of the antigen and antibody is measured.

In an automated analyzing apparatus used hitherto for biochemical tests, the possiblity that a sample solution such as a serum of a patient may become turbid due to the presence of colloidal particles attributable to a disease is taken into consideration, and the optical system thereof is so designed that the measured value may not be adversely affected by the turbidity of the sample. Therefore, the prior art automated analyzing apparatus is not primarily suitable for sensing the turbidity of the reaction solution attributable to the formation of the combined product of the antigen and antibody by the immunoreaction.

It is therefore a primary object of the present invention to provide an automated analyzing apparatus capable of measurement both of the immunity-related tests and the biochemical tests.

In accordance with the present invention, there is provided a photometer including an entrance slit permitting passing therethrough of the entirety or a portion of a convergent light beam transmitted successively through a plurality of sample measurement cells each containing a sample solution therein and a sensor converting the quantity of light passed through the entrance slit into a physical quantity which is an objective of measurement, the photometer comprising a scattered light sensor disposed between the sample measurement cells and the entrance slit at a position where the sensor is not irradiated with a straight advancing component of the light beam.

The present invention will be apparent from the following detailed description taken in conjunction with the accompanying drawings, in which.

Figure 1:
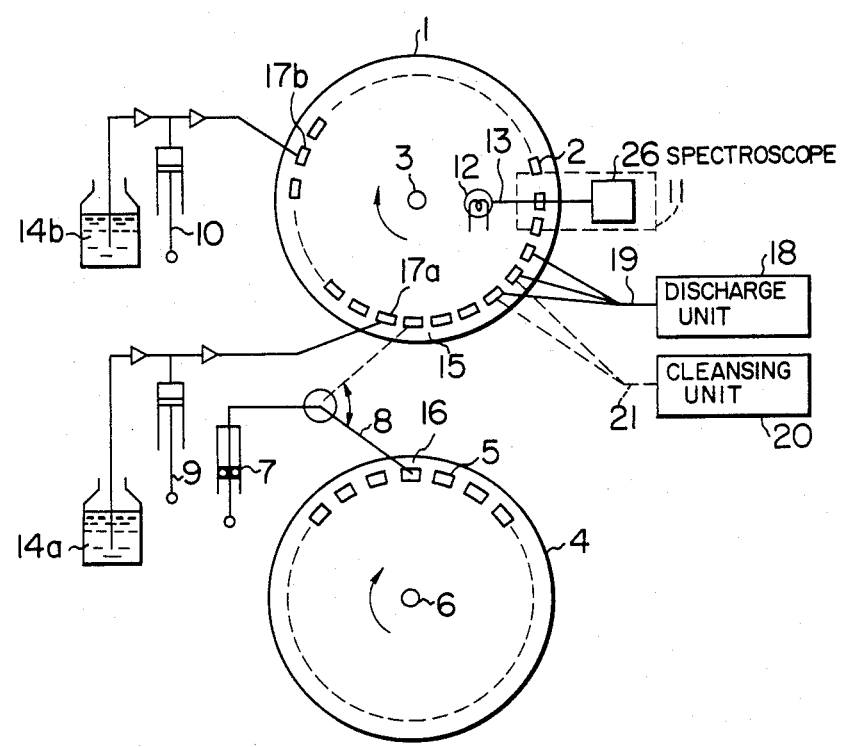
FIG. 1 is a diagrammatic plan view of a preferred embodiment of the present invention.

Referring now to the drawings, FIG. 1 shows diagrammatically the structure of a preferred embodiment of the automated analyzing apparatus according to the present invention. Referring to FIG. 1, a reaction disc 1 is provided, adjacent to its circumferential edge, with a plurality of (for example, 40) equally circumferentially spaced, sample measurement cells 2 and is rotated clockwise intermittently around a rotary axis 3. A sample table 4 is also provided, adjacent to its circumferential edge, with a plurality of equally circumferentially spaced, sample containers 5 and is similarly rotated clockwise around a rotary axis 6. Sample solutions are transferred from the sample containers 5 to the measurement cells 2 by the combination of a pipetter 7 and a sampling probe 8, and necessary reagents are dispensed by dispensers 9 and 10. That is, a first reagent 14a is dispensed into the measurement cells 2 at a first dispensing position 17a by the first dispenser 9, and a second reagent 14b is dispensed into the measurement cells 2 at a second dispensing position 17b by the second dispenser 10.

A light beam 13 emitted from a light source 12 which is a white lamp passes through the measurement cell 2 brought to the position opposite thereto and is then incident upon a spectrophotometer 11. The light beam 13 transmits through the measurement cell 2 when the reaction disc 1 is halted temporarily during its intermittent rotation. A solution discharge tube 19 and a cell cleansing tube 21 are disposed between the cell transmitting position of the light beam 13 and a sample injecting position 15. The sample solution contained in the measurement cell 2 having been subjected to the measurement is discharged from a solution discharge unit 18 after flowing through the discharge tube 19. Then, cell cleaning water supplied from a cell cleansing unit 20 is injected through the cleansing tube 21 into the measurement cell 2 to cleanse the interior of the same. The reference numeral 16 designates a specific position at which the aliquot of a sample solution contained in the sample container 5 on the sample table 4 is pipetted out by the sampling probe 8. This sampling probe 8 makes a reciprocatory swinging movement between the sample pipetting position 16 and the sample discharging position 15 to place the sample solution into the measurement cell 2. At this time, both the sample table 4 and the reaction disc 1 are halted temporarily.

Figure 2:
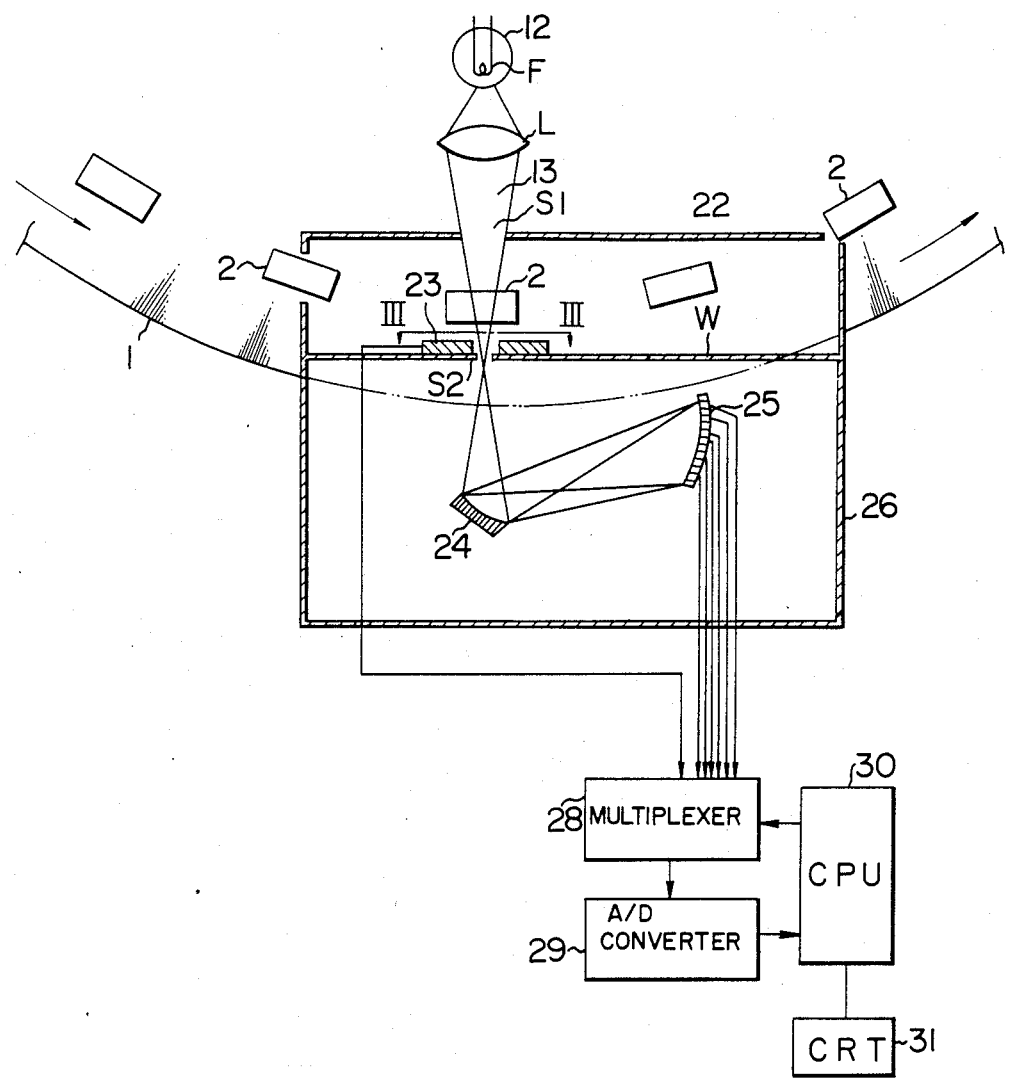
FIG. 2 is a partly sectional, enlarged plan view showing in detail the structure of the spectrophotometer shown in FIG. 1, together with a block diagram of a signal processing circuit.

FIG. 2 is a block diagram showing in detail the structure of the photometric system in the apparatus shown in FIG. 1. In FIG. 2, the same reference numerals are used to designate the same parts appearing in FIG. 1. Referring to FIG. 2, the light beam 13 emitted from the white lamp 12 is condensed by a condenser lens L, and the convergent light beam 13 is incident upon one of the measurement cells 2 in a sample chamber 22 which is in the form of a dark box, after passing through a first entrance slit $S_1$ formed in the outer wall of the chamber 22. The light beam 13 transmitted through this measurement cell 2 passes then through an elongate second slit $S_2$ formed in the partition wall W partitioning the sample chamber 22 from a spectroscope 26, and is incident upon a concave diffraction grating 24 to be diffracted thereby forming a spectral image on a photodiode array type of photosensor 25 capable of simultaneous measurement of a plurality of wavelengths. The spectroscope 26 is also in the form of a dark box, and its inner surface is coated with, for example, a black delustering paint so as to minimize internal reflection of light. Such a spectroscope 26 is commonly known in this field of art and is disclosed in, for example, U.S. Pat. No. 4,313,735.

Figure 3:
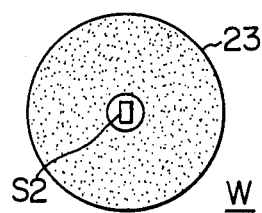
FIG. 3 is a schematic plan view showing the shape of the scattered light sensor and its positional relationship with the entrance slit in the embodiment shown in FIG. 1.

An annular, scattered light sensor 23 is mounted around and adjacent to the second entrance slit $S_2$ in a manner as shown in FIG. 3. This sensor 23 senses light scattered forward within a suitable angular range by the measurement cell 2. The output signals from the transmitted light sensor 25 and scattered light sensor 23 are applied to a multiplexer 28 after preferably being amplified by associated amplifiers (not shown) and are then converted into digital signals by an A/D converter 29. The digital signals from the A/D converter 29 are processed by central processor unit (CPU) 30 to be displayed on a suitable display means, for example, a CRT display 31. In the case of measurement of biochemical tests, the photodiodes sensing two kinds of predetermined light wavelengths close to each other are only scanned under command of the CPU 30, and the output signals from such photodiodes are processed. That is, two-wavelength photometry is made in the case of measurement of biochemical tests. A processing system for processing individual output signals from such sensors is already commonly known per se and is disclosed in, for example, U.S. Pat. No. 4,263,512.

FIG. 3 is an enlarged plan view of the scattered light sensor 23. It will be seen in FIG. 3 that this sensor 23 is annular in shape and has an outer diameter of about 10 mm and an inner diameter of about 2 mm, and the second entrance slit $S_2$ formed in the partition wall W is shown disposed in the central opening of the sensor 23. This scattered light sensor 23 may be a photocell, a silicon diode or the like widely used in this field of art.

Figure 4:
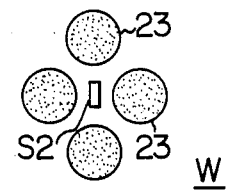
FIG. 4 is a schematic plan view showing a variation of the scattered light sensors.

The shape of the scattered light sensor 23 is in no way limited to that shown in FIG. 3, and the desired object of the present invention can be similarly attained even when a sensor type as shown in FIG. 4 may be used. It will be seen in FIG. 4 that a plurality of such sensors 23 are disposed around and adjacent to the second entrance slit $S_2$. The scattered light sensor or sensors 23 may be fixed directly to the surface of the partition wall W or fixed at a position spaced from such a surface.

The second entrance slit $S_2$ has an elongate shape because the optical image of the filament F of the light source 12 has an elongate shape attributable to the structure of the filament F. Thus, the shape of this second entrance slit $S_2$ is dependent upon the shape of the optical image of the filament F of the light source 12.

The procedure for operation of the automated analyzing apparatus having the aforementioned structure will now be outlined. Referring to FIG. 1, the plural measurement cells 2 are mounted in the predetermined positions on the reaction disc 1, and the sample containers 5 containing sample solutions to be examined are mounted in the predetermined positions on the sample table 4. The pipetter 7 is actuated to draw out the sample solution contained in the sample container 5 brought now to the sample drawing position 16 and to feed it into the sampling probe 8. Then, the sampling probe 8 is swung to the position opposite to the measurement cell 2 brought now to the sample injecting position 15 to place a predetermined quantity of the sample solution into the measurement cell 2. The above operation is effected while both the sample table 4 and the reaction disc 1 are halted temporarily during intermittent rotation.

When the measurement cell 2 having the sample solution injected therein is brought to the first reagent dispensing position 17a after the reaction disc 1 makes its one complete revolution plus one pitch clockwise, the first dispenser 9 is actuated to draw out a predetermined quantity of the first reagent 14a and to add it to the sample solution into the measurement cell 2. Then, when the measurement cell 2 is brought to the second reagent dispensing position 17b, the second dispenser 10 is actuated to draw out a predetermined quantity of the second reagent 14b and to add it to the mixture of the sample solution and the first reagent 14a in the measurement cell 2. The reaction disc 1 is rotated through 360° plus 1 pitch in each cycle so that its position is shifted by 1 pitch after each cycle, and the operation of the reaction disc 1 is, for example, such that it is kept halted for 9.5 sec and rotated for 20.5 sec to complete one cycle of 30 sec. Therefore, the transmittance of the reaction solution and the intensity of light scattered by the reaction solution are measured respectively at a time interval of 30 sec to compute the reaction speeds of the analyzed components contained in the sample solution thereby enabling the quantitative analysis of the components.

By the above analytical procedure, the analysis of biochemical tests according to the end point method and rate method and the analysis of immunochemical tests according to the light scattering method are both efficiently effected. That is, from the photometrical aspect, both the transmittance photometry mode and the scattered light photometry mode are effected.

Therefore, the single automated analyzing apparatus for biochemical tests can perform the two modes of photometry with high accuracy without the necessity for additional provision of any special apparatus.

Table 1 shows examples of reagents used for the measurement of biochemical tests and immunity-related tests based on the principle of photometry above described. More specifically, Table 1 shows examples of reagents when glutamate-oxaloacetate transaminase (GOT) and immunoglobulin G (IgG) were measured as a biochemical tests and an immunity-related tests respectively.

TABLE 1

| | | | |
|---|---|---|---|
| 1. | GOT | | |
| | First reagent | MDH | 845 U/ml |
| | | LDH | 208 U/ml |
| | | NADH | 0.24 mM (Millimole) |
| | | l-aspartate acid | 41 mM |
| | | Tris buffer solution (pH 8.5) | 0.01 mM |
| | Second reagent | α-ketoglutarate | 3.3 mM |
| | | Phosphate buffer solution (pH 7.2) | 0.5 M (mole/l) |
| 2. | IgG | | |
| | First reagent | Human IgG antibody (ovine) | 10 mM |
| | | Barbital buffer solution (pH 7.2) | |
| | | Sodium chloride | 0.88 wt % |
| | | Sodium azide | 0.1 wt % |
| | | Polyethylene glycol 6000 | small quantity |

Table 2 shows the analytical conditions of measurement of the tests shown in Table 1.

TABLE 2

| Item | GOT | IgG |
|---|---|---|
| Quantity of sample | 20 μl | 20 μl |
| Quantity of first reagent | 400 μl | 500 μl |
| Quantity of second reagent | 100 μl | 0 |
| Measuring wavelength 1 | 376 nm | — |
| Measuring wavelength 2 | 340 nm | 632.8 nm |
| Reaction temperature | 37° C. | 37° C. |

Table 3 shows the results of measurement when both of the biochemical tests and the immunity-related tests were measured under the analytical conditions shown in Table 2. In Table 3, reagents used in the laser nephelometry were applied on the measurement of the immunity-related tests.

TABLE 3

| Sample No. | Tests | Found value |
|---|---|---|
| 1 | GOT | 94 |
| | GPT | 43 |
| | IgG | 450 |
| | IgA | 521 |
| | IgM | 328 |
| 2 | GOT | 48 |
| | GPT | 22 |
| | CRP | 3.2 |
| 3 | GOT | 52 |
| | GPT | 24 |
| | RA | 24.6 |
| | CRP | 2.8 |
| 4 | CHO | 168 |
| | GOT | 51 |
| | GPT | 25 |
| | IgG | 350 |

In Table 3, GPT, IgA, IgM, CRP, RA and CHO are abbreviations of glutamate-pyruvate transaminase, immunoglubulin A, immunoglobulin M, C-reactive protein, rheumatoid antigen arthritis factor, and cholesteral respectively. Remarks: The units of the found values are as follows:

GOT, GPT . . . mU/ml
CHO . . . mg/dl
GRP, IgG, IgA, IgM . . . mg/dl
RA . . . U/ml

It was thus confirmed that mesurement of both of biochemical tests and immunity-related tests, which could not be measured by the prior art automated analyzing apparatus, could be achieved by the automated analyzing apparatus of the present invention. The immunity-related tests which were confirmed to be measurable together with biochemical tests are as follows:

IgG, IgA, IgM, complement 3 ($C_3$), complement 4 ($C_4$), CRP, RA, fibrinogen, transferin and $\alpha_1$-antitripsin It can be expected that the number of measurable immunity-related tests can be further increased when reagents usable for the quantitative analysis of such tests based on the scattered light photometry are further developed in future.

The imprecision was ascertained by repeating measurement of IgG twenty times on the same sample, and the results of measurement are shown in Table 4.

TABLE 4

| Measurement No. | Measured value of IgG |
|---|---|
| 1 | 1630 |
| 2 | 1590 |
| 3 | 1650 |
| 4 | 1660 |
| 5 | 1710 |
| 6 | 1630 |
| 7 | 1640 |
| 8 | 1670 |
| 9 | 1610 |
| 10 | 1680 |
| 11 | 1650 |
| 12 | 1600 |
| 13 | 1640 |
| 14 | 1680 |
| 15 | 1660 |
| 16 | 1670 |
| 17 | 1580 |
| 18 | 1650 |
| 19 | 1600 |
| 20 | 1680 |

Remarks: The unit of measured values of IgG is mg/dl.

According to the results of measurement of IgG shown in Table 4, the standard deviation (SD) is 3.36 and the coefficient variation (CV) is 2.05%. These values of SD and CV are substantially compatible with the results of measurement of imprecision in an experiment using the laser nephelometer. Further, in regard to the working curve too, the results of measurement are similar to those obtained by the laser nephelometer, as shown in FIG. 5.

Figure 5:
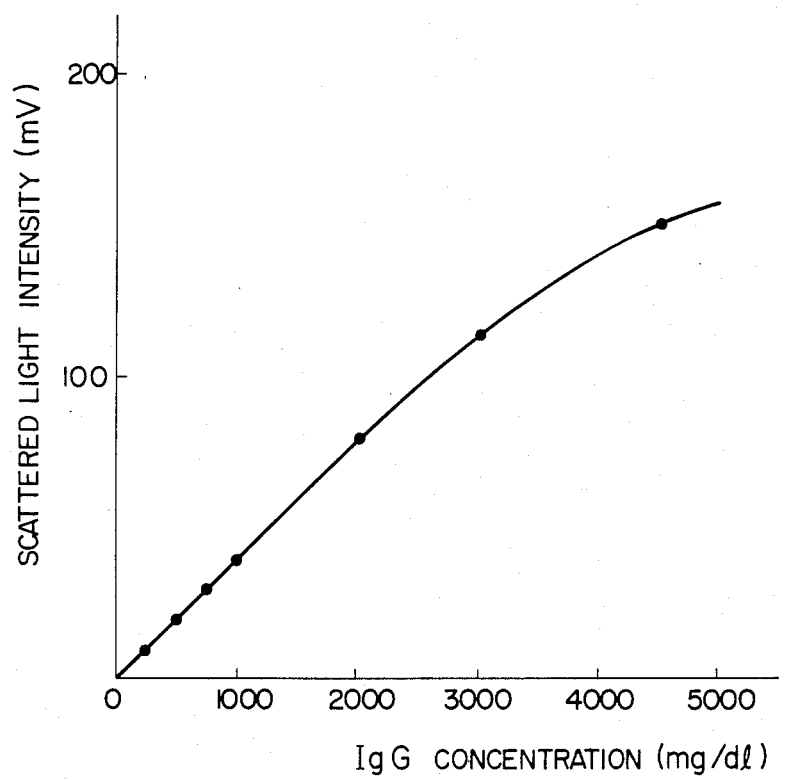
FIG. 5 is a graph showing the relation between the measured concentration of IgG and the intensity of scattered light.

FIG. 5 is a graph showing the relation between the concentration of IgG and the intensity of Scattered light. In FIG. 5, the horizontal axis represents the concentration of IgG in mg/dl, and the vertical axis represents the intensity of scattered light in mV. It will be seen in FIG. 5 that the curve is rectilinear up to at least the IgG concentration of 2000 mg/dl.

Although a spectrophotometer using a white lamp as its light source is shown as one form of the embodiment, the present invention is in no way limited to such a spectrophotometer. That is, the light source used for the purpose of measurement may be a lamp emitting a monochromatic light beam having a specific wavelength or the combination of a white lamp and a filter transmitting a specific wavelength only, so that both the transmittance and the scattered light intensity can be measured by a conventional photometer without separation of light into its spectral components as in the aforementioned embodiment.

Further, in the aforementioned embodiment, the transmittance of the reaction solution and the intensity of light scattered by the reaction solution are not simultaneously measured but are alternately measured at a time interval of about 30 sec. However, when the transmittance and the scattered light intensity are measured substantially simultaneously, a measurement error of the transmittance can be corrected on the basis of the measured value of the intensity of light scattered by the reaction solution so that the transmittance can be more accurately determined.

Another embodiment or a modification of the present invention in which the transmittance is corrected on the basis of the measured value of the scattered light intensity will now be described in detail.

In the absorptiometry, light is directed to a sample solution, and the rate of light absorption at a point spaced a predetermined distance on the optical path from the light source is measured to measure the transmittance, as is commonly known in this field of art. In the spectro-photometer according to the present invention too, light from the sample container 2 can be introduced into the photometer so as to measure the transmittance on the basis of the quantity of introduced light. However, as is well known, it is the absolute condition of the absorptiometry that the sample solution in the sample container 2 be transparent or permeable to light. This is because, if particles enough to cause scattering of light were present in the sample solution, the scattered light would be regarded as if it were absorbed by the solute in the sample solution, and a positive error would result in the measurement according to the absorptiometry.

This problem is frequently encountered during measurement of a lipemic serum found in serums handled in, for example, clinical laboratories. (The term "lipemic serum" designates generally a milky serum which becomes turbid or muddy due to a high concentration of lipid substances in the serum.)

Figure 6:
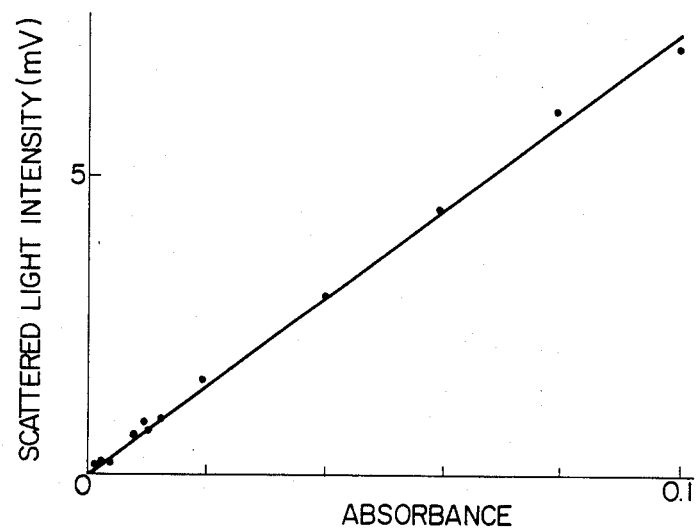
FIG. 6 is a graph showing the relation between the transmittance and the scattered light intensity measured on the same sample.
Figure 7:
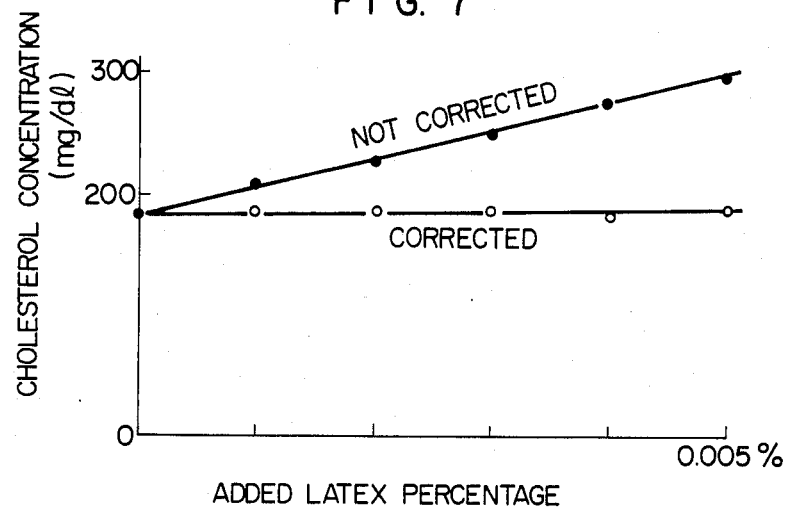
FIG. 7 is a graph showing the relation between the quantity of added latex particles and the measured concentration of cholesterol.

In an effort to solve the above problem by the use of the photometer according to the present invention, the inventors of the present application have made researches and studies and found that the output signal of the photometer can be corrected on the basis of the output signal of the sensor 23 provided for measuring the intensity of scattered light. FIG. 6 shows the relation between the transmittance and the scattered light intensity (indicated by the output signal of the sensor 23) experimentally determined on various lipemic serums. FIG. 7 shows the results of an experiment in which the measured values of cholesterol in various serums are corrected utilizing the relation shown in FIG. 6. In this experiment, fine particles of latex having a diameter of 0.114$\mu$ were used to provide turbidity. It will be apparent from FIG. 7 that the transmittance-representing output signal of the photometer can be corrected on the basis of the output signal of the scattered light sensor 23 appearing together with the former output signal.

We claim:

1. An automated analyzing apparatus comprising:
   a sample chamber having an optical path therein, said sample chamber being arranged for receiving a row of measurement cells passing across the optical path, each measurement cell being arranged for receiving at least a sample to be analyzed;
   a spectroscope disposed adjacent to said sample chamber, said spectroscope having an entrance slit;
   light source means for providing white light for illuminating said measurement cell within said sample chamber, light from said light source means passing along the optical path of said sample chamber through said measurement cell so as to be incident in said spectroscope through said entrance slit and being scattered by a grating into first detector means arranged for detecting a plurality of individual light wavelengths and for providing an output indicative thereof;
   second detector means for detecting scattering light scattered from said measurement cell upon illumination of said measurement cell by said light source means, said second detector means being disposed within said sample chamber so as to surround said entrance slit and providing an output of the detected scattering light; and
   means for calculating the concentration of components of said sample in said measuring cell on the basis of the output of said first detector means, said calculating means being responsive to the output of said second detector means for compensating the calculated concentration so as to substantially eliminate an error in the calculated concentration due to turbidity of said sample.

2. An automated analyzing apparatus according to claim 1, wherein qunatities of light transmitted through and scattered by said sample in the illuminated measurement cell are sensed by said first detector means and said second detector means, respectively, and data obtained from said second detector means is utilized to correct data obtained from said first detector means.

3. An automated analyzing apparatus according to claim 1, wherein said second detector means is an annular scattering light sensor, and said entrance slit of said spectroscope is disposed in a central opening of said annular scattering light sensor.

4. An automated analyzing appratus according to claim 1, wherein said second detector means includes a plurality of photocells disposed around and adjacent to said entrance slit of said spectroscope.

5. An automated analyzing apparatus according to claim 1, wherein said second detector means is fixed to a wall in which said entrance slit of said spectroscope is disposed.

6. An automated analyzing apparatus according to claim 1, wherein said sample chamber is a dark box isolated substantially from external ambient light, said row of measurement cells moving through said dark box.

7. An automated analyzing apparatus according to claim 1, further comprising means for injecting samples into said measurement cells, and means for dispensing necessary reagents into said measurement cells.

* * * * *